United States Patent
Aoyama

(10) Patent No.: US 12,089,805 B2
(45) Date of Patent: *Sep. 17, 2024

(54) MEDICAL IMAGE PROCESSING APPARATUS AND ENDOSCOPE APPARATUS

(71) Applicant: FUJIFILM Corporation, Tokyo (JP)

(72) Inventor: Tatsuya Aoyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/063,683

(22) Filed: Dec. 9, 2022

(65) Prior Publication Data

US 2023/0119040 A1 Apr. 20, 2023

Related U.S. Application Data

(63) Continuation of application No. 16/847,674, filed on Apr. 14, 2020, now Pat. No. 11,574,401, which is a (Continued)

(30) Foreign Application Priority Data

Oct. 17, 2017 (JP) .................................. 2017-201333

(51) Int. Cl.
*A61B 1/00* (2006.01)
*A61B 1/06* (2006.01)
(Continued)

(52) U.S. Cl.
CPC ...... *A61B 1/000094* (2022.02); *A61B 1/0638* (2013.01); *A61B 5/7275* (2013.01); (Continued)

(58) Field of Classification Search
CPC ............ A61B 1/000094; A61B 1/0638; A61B 5/7275; G06T 7/0012; G06T 2207/10068; G06T 2207/30096
See application file for complete search history.

(56) References Cited

U.S. PATENT DOCUMENTS 8,913,111 B2 * 12/2014 Takahashi .......... G02B 23/2476
348/65
9,654,745 B2 * 5/2017 Zeng ................ A61B 1/000096
(Continued)

FOREIGN PATENT DOCUMENTS

KR 101762678 B1 * 8/2017 ............. G06T 7/136

OTHER PUBLICATIONS

Aranzazu Jauregui-Amezaga, Auke Geerits, Yannick Das, Bart Lemmens, Xavier Sagaert, Talat Bessissow, Triana Lobatón, Marc Ferrante, Gert Van Assche, Raf Bisschops, Karel Geboes, Gert De Hertogh, Séverine Vermeire, a Simplified Geboes Score for Ulcerative Colitis, Journal of Crohn's and Colitis, (Year: 2016).*
(Continued)

*Primary Examiner* — Aaron W Carter
*Assistant Examiner* — Courtney Joan Nelson
(74) *Attorney, Agent, or Firm* — JCIPRNET

(57) ABSTRACT

A medical image processing apparatus includes a processor configured to acquire a medical image including a subject image; perform a first discrimination process of detecting a lesion and discriminating a degree of progress of the detected lesion by using a first medical image captured using first illumination light having a specific spectrum, among the medical images; and perform a second discrimination process of discriminating the degree of progress of the lesion by using a second medical image captured using second illumination light having a spectrum different from the first illumination light, among the medical images, wherein the processor performs the second discrimination process in a case where a type of the lesion detected in the first discrimination process is a specific type, or in a case where the lesion detected in the first discrimination process indicates a specific degree of progress.

11 Claims, 9 Drawing Sheets

Related U.S. Application Data continuation of application No. PCT/JP2018/038496, filed on Oct. 16, 2018.

(51) Int. Cl.
 *A61B 5/00* (2006.01)
 *G06T 7/00* (2017.01)

(52) U.S. Cl.
 CPC .. *G06T 7/0012* (2013.01); *G06T 2207/10068* (2013.01); *G06T 2207/30096* (2013.01)

(56) References Cited

U.S. PATENT DOCUMENTS

| | | | | |
|---|---|---|---|---|
| 2007/0055105 | A1* | 3/2007 | Matsuzawa | A61B 1/00096 600/176 |
| 2012/0302847 | A1* | 11/2012 | Ozawa | A61B 1/063 600/339 |
| 2013/0018242 | A1* | 1/2013 | Yamaguchi | A61B 1/0638 600/339 |
| 2016/0022126 | A1* | 1/2016 | Ramesh | A61B 1/0638 600/109 |

OTHER PUBLICATIONS

[continuation of item U]: vol. 11, Issue 3, Mar. 2017, pp. 305-313, https://doi.org/10.1093/ecco-jcc/jw154 (Year: 2016).*

Machine translation of KR 101762678 B1 (obtained from PE2E Search) (Year: 2017).*

D. Glotsos et al., "A hierarchical decision tree classification scheme for brain tumour astrocytoma grading using support vector machines," 3rd International Symposium on Image and Signal Processing and Analysis, 2003. ISPA 2003. Proceedings of the, Rome, Italy, 2003, pp. 1034-1038 vol. 2, (Year: 2003).*

* cited by examiner

FIG. 4

| FIRST DISCRIMINATION PROCESS | SECOND DISCRIMINATION PROCESS |
|---|---|
| Mayo 3 | - |
| Mayo 2 | - |
| Mayo 1 | Mayo 1-III |
| Mayo 1 | Mayo 1-II |
| Mayo 1 | Mayo 1-I |
| Mayo 0 | Mayo 0-III |
| Mayo 0 | Mayo 0-II |
| Mayo 0 | Mayo 0-I |

MEDICAL IMAGE PROCESSING APPARATUS AND ENDOSCOPE APPARATUS

CROSS-REFERENCE TO RELATED APPLICATIONS

This application is a Continuation Application of U.S. application Ser. No. 16/847,674 filed on 14 Apr. 2020, which is a Continuation of PCT International Application No. PCT/JP2018/038496 filed on 16 Oct. 2018, which claims priority under 35 U.S.C § 119(a) to Japanese Patent Application No. 2017-201333 filed on 17 Oct. 2017. The above application is hereby expressly incorporated by reference, in its entirety, into the present application.

BACKGROUND OF THE INVENTION

1. Field of the Invention

The present invention relates to a medical image processing apparatus that uses analysis results of medical images, and an endoscope apparatus.

2. Description of the Related Art

In the related art, an apparatus that acquires an image including a subject image (hereinafter, referred to as a medical image) among apparatuses relevant to medical care (hereinafter, referred to as a medical apparatus) presents the acquired medical image to a doctor. Then, the doctor performs diagnosis or the like using the medical image obtained from the medical apparatus as one of determination materials. Needless to say, discrimination of a state of the subject or the like that is performed using the medical image at the time of diagnosis is based on skill, experience, and the like of the doctor.

In recent years, since image analysis technology has advanced, objective information or quantitative information can be acquired from the medical image by analyzing the medical image. For this reason, the medical apparatus that supports discrimination, diagnosis, and the like by presenting an analysis result of the medical image to a doctor or the like has been on the increase. For example, an endoscope apparatus disclosed in JP2006-198106A (corresponding to US2008/0009669A1) specifies a position of an abnormal region by using a fluorescence image captured using fluorescence or a narrow-band light image captured using light having a specific narrow wavelength band (a so-called narrow-band light). Then, the position of the abnormal region is displayed in an endoscopic image for display.

SUMMARY OF THE INVENTION

In the medical apparatus of the related art, the medical image is analyzed to detect a region to be noted (a region referred to as a so-called region of interest, attention region, or abnormal region, hereinafter simply referred to as a lesion or the like) including one or a plurality of portions in which an abnormality such as a lesion is recognized (a lesion portion or a portion possibly having a lesion) and the position or the like is presented to support diagnosis or the like.

A doctor or the like discriminates a type and a degree of progress of a lesion or the like presented by the medical apparatus, but discrimination of the type and the degree of progress of a lesion or the like is still a heavy burden. For this reason, in recent years, in order to further reduce the burden on a doctor or the like, it has been required to provide detailed information that serves as a material for discrimination regarding the type and the degree of progress of a lesion or the like.

An object of the present invention is to provide a medical image processing apparatus and an endoscope apparatus that can present more detailed information regarding a lesion or the like than before.

A medical image processing apparatus of the present invention comprises: a medical image acquisition unit that acquires a medical image including a subject image; a first discrimination processing unit that performs a first discrimination process of detecting a lesion and discriminating a degree of progress of the detected lesion by using a first medical image captured using first illumination light having a specific spectrum, among the medical images; and a second discrimination processing unit that performs a second discrimination process of discriminating the degree of progress of the lesion by using a second medical image captured using second illumination light having a spectrum different from the first illumination light, among the medical images.

It is preferable that the medical image processing apparatus further comprises a storage unit that stores a combination of the first illumination light and the second illumination light in advance.

It is preferable that the combination of the first illumination light and the second illumination light is determined based on a type of the lesion detected in the first discrimination process or the degree of progress of the lesion detected in the first discrimination process.

It is preferable that the second medical image is the medical image captured using the second illumination light having a narrower wavelength band than the first illumination light.

It is preferable that the second medical image is the medical image captured using the second illumination light with more specific blue or specific violet than the first illumination light.

It is preferable that the first medical image is the medical image captured using white light.

It is preferable that the first discrimination processing unit detects an inflammatory bowel disease or a cancer as the lesion.

It is preferable that the second discrimination processing unit performs the second discrimination process in a case where a type of the lesion detected in the first discrimination process is a specific type, or in a case where the lesion detected in the first discrimination process indicates a specific degree of progress.

It is preferable that in a case where the second discrimination processing unit performs the second discrimination process, a result of the second discrimination process is output as a final discrimination result, and in a case where the second discrimination processing unit does not perform the second discrimination process, a result of the first discrimination process is output as a final discrimination result.

It is preferable that in a case where the first discrimination processing unit detects ulcerative colitis as the lesion and discriminates a grade of an endoscopic finding classification as a degree of progress of the ulcerative colitis, the second discrimination processing unit performs the second discrimination process in a case where the grade of the ulcerative colitis is a specific grade.

It is preferable that the second discrimination processing unit outputs a discrimination result obtained by further subdividing the grade of the endoscopic finding classification.

It is preferable that in a case where the first discrimination processing unit discriminates a grade of a Mayo classification as the degree of progress of the ulcerative colitis, the second discrimination processing unit does not perform the second discrimination process in a case where the degree of progress of the ulcerative colitis is grade 2 or grade 3, and performs the second discrimination process in a case where the degree of progress of the ulcerative colitis is grade 0 or grade 1.

It is preferable that in a case where the first discrimination processing unit discriminates a grade of a Matts classification as the degree of progress of the ulcerative colitis, the second discrimination processing unit does not perform the second discrimination process in a case where the degree of progress of the ulcerative colitis is grade 3 or more, and performs the second discrimination process in a case where the degree of progress of the ulcerative colitis is grade 1 or grade 2.

It is preferable that in a case where the first discrimination processing unit detects a cancer as the lesion, the second discrimination processing unit does not perform the second discrimination process in a case where the lesion detected in the first discrimination process is not a cancer, and performs the second discrimination process in a case where the cancer is detected in the first discrimination process.

It is preferable that the second discrimination processing unit outputs information related to prediction of a treatment effect as a discrimination result.

An endoscope apparatus of the present invention comprises: a light source unit that emits a plurality of types of illumination light having different spectra; an endoscopic image acquisition unit that acquires an endoscopic image including a subject image by imaging a subject using the illumination light; a first discrimination processing unit that performs a first discrimination process of detecting a lesion and discriminating a degree of progress of the detected lesion by using a first endoscopic image captured using first illumination light having a specific spectrum, among the endoscopic images; a light source control unit that switches the illumination light to a second illumination light having a different spectrum from the first illumination light in accordance with a type or the degree of progress of the lesion; and a second discrimination processing unit that performs a second discrimination process of discriminating the degree of progress of the lesion by using a second endoscopic image captured using the second illumination light.

The medical image processing apparatus and the endoscope apparatus of the present invention can provide more detailed information regarding a lesion or the like than before.

BRIEF DESCRIPTION OF THE DRAWINGS

FIG. 4 is a table showing a relationship between a classification of a first discrimination process and a classification of a second discrimination process.

DESCRIPTION OF THE PREFERRED EMBODIMENTS

First Embodiment

Figure 1:
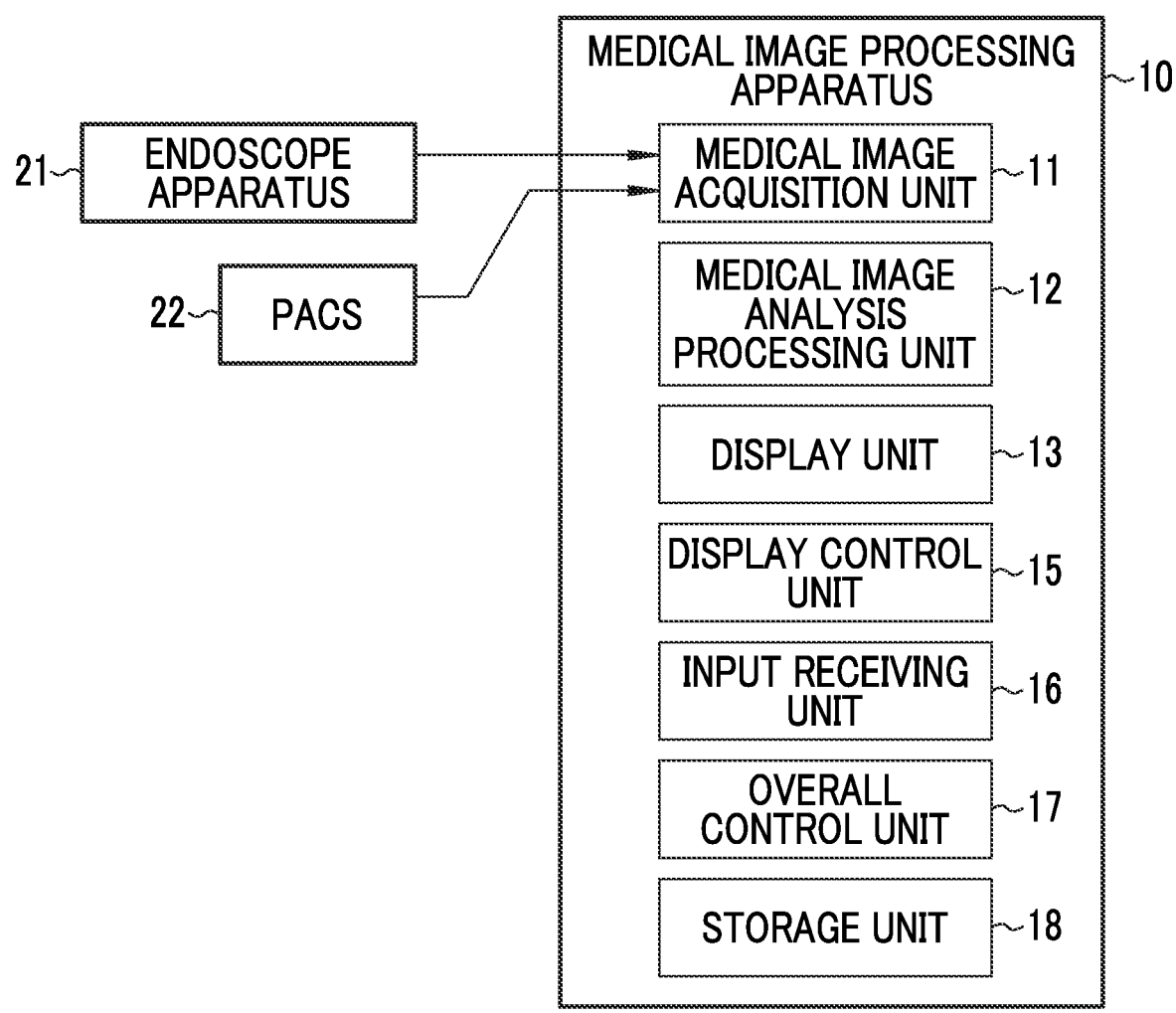
FIG. 1 is a block diagram of a medical image processing apparatus.

As shown in FIG. 1, a medical image processing apparatus 10 comprises a medical image acquisition unit 11, a medical image analysis processing unit 12, a display unit 13, a display control unit 15, an input receiving unit 16, an overall control unit 17, and a storage unit 18.

The medical image acquisition unit 11 acquires a medical image including a subject image, directly from an endoscope apparatus 21 or the like that is a medical apparatus, or through a management system such as a picture archiving and communication system (PACS) 22, or other information systems. The medical image is a still image or a motion picture (a so-called examination motion picture). In a case where the medical image is a motion picture, the medical image acquisition unit 11 can acquire a frame image forming a motion picture after examination as a still image. In addition, in a case where the medical image is a motion picture, display of the medical image includes not only displaying a still image of one representative frame forming the motion picture but also reproducing the motion picture once or multiple times. In addition, the medical image acquired by the medical image acquisition unit 11 includes an image automatically captured by a medical apparatus such as the endoscope apparatus 21 regardless of a capturing instruction of a doctor, in addition to an image captured by a doctor using a medical apparatus such as the endoscope apparatus 21.

In the case of being capable of acquiring a plurality of medical images, the medical image acquisition unit 11 can selectively acquire one or a plurality of medical images among these medical images. In addition, the medical image acquisition unit 11 can acquire a plurality of medical images acquired in a plurality of different examinations. For example, it is possible to acquire one or both of a medical image acquired in an examination performed in the past and a medical image acquired in the latest examination. That is, the medical image acquisition unit 11 acquires a medical image optionally.

In the present embodiment, the medical image processing apparatus 10 is connected to the endoscope apparatus 21 to acquire a medical image from the endoscope apparatus 21. That is, in the present embodiment, the medical image is an endoscopic image.

In a case where detection of a lesion or the like and discrimination of a degree of progress of a lesion or the like are performed, the medical image acquisition unit 11 acquires at least one or a plurality of endoscopic images (medical images) having different imaging conditions. Specifically, in the present embodiment, the medical image acquisition unit 11 acquires one or a plurality of first endoscopic images 111 (see FIG. 7) for detecting a lesion or the like, and roughly discriminating the degree of progress of the detected lesion or the like. Further, the medical image acquisition unit 11 acquires one or a plurality of second endoscopic images 121 (see FIG. 8) for discriminating the degree of progress of the lesion or the like in detail, as necessary.

The imaging condition is a condition relating to imaging of a medical image, and is, for example, the spectrum of illumination light, the presence or absence or intensity of image processing at the time of generating a medical image, and the like. The spectrum of the illumination light is an intensity distribution for each wavelength, and includes the concept of a wavelength band and a center wavelength. The image processing at the time of generating a medical image is, for example, processing related to adjustment of a color or the like that emphasizes a specific tissue, lesion, or the like. In addition to the above, in the present embodiment, the medical image acquisition unit 11 acquires an endoscopic image 101 for display to be displayed on the display unit 13 (see FIG. 6). In many cases, the imaging condition of the endoscopic image 101 for display is different from those of the first endoscopic image 111 used for detecting a lesion or the like and roughly discriminating the degree of progress of the lesion or the like, and the second endoscopic image 121 used for discriminating the lesion or the like in detail. Here, depending on the type or the degree of progress of the detected lesion or the like, the endoscopic image 101 for display can be used for detection of the lesion or the like, rough discrimination of the degree of progress of the lesion or the like, or detailed discrimination of the lesion or the like. In the present embodiment, as an example, an example is shown in which ulcerative colitis is detected as a lesion or the like. Therefore, the medical image acquisition unit 11 acquires the first endoscopic image 111 for rough discrimination separately from the endoscopic image 101 for display, but these are all endoscopic images obtained by imaging a subject using white light, and are of substantially the same type.

Note that the medical image acquired by the medical image acquisition unit 11 in the present embodiment is a medical image captured in one specific examination. In addition, a medical image acquired for a portion for detecting a lesion or the like and discriminating the degree of progress is, in principle, a series of medical images captured within a temporal range in which the angle of view, the shape of a subject, and the like do not significantly change (within a temporal range in which portions can be associated with each other in image processing).

Figure 2:
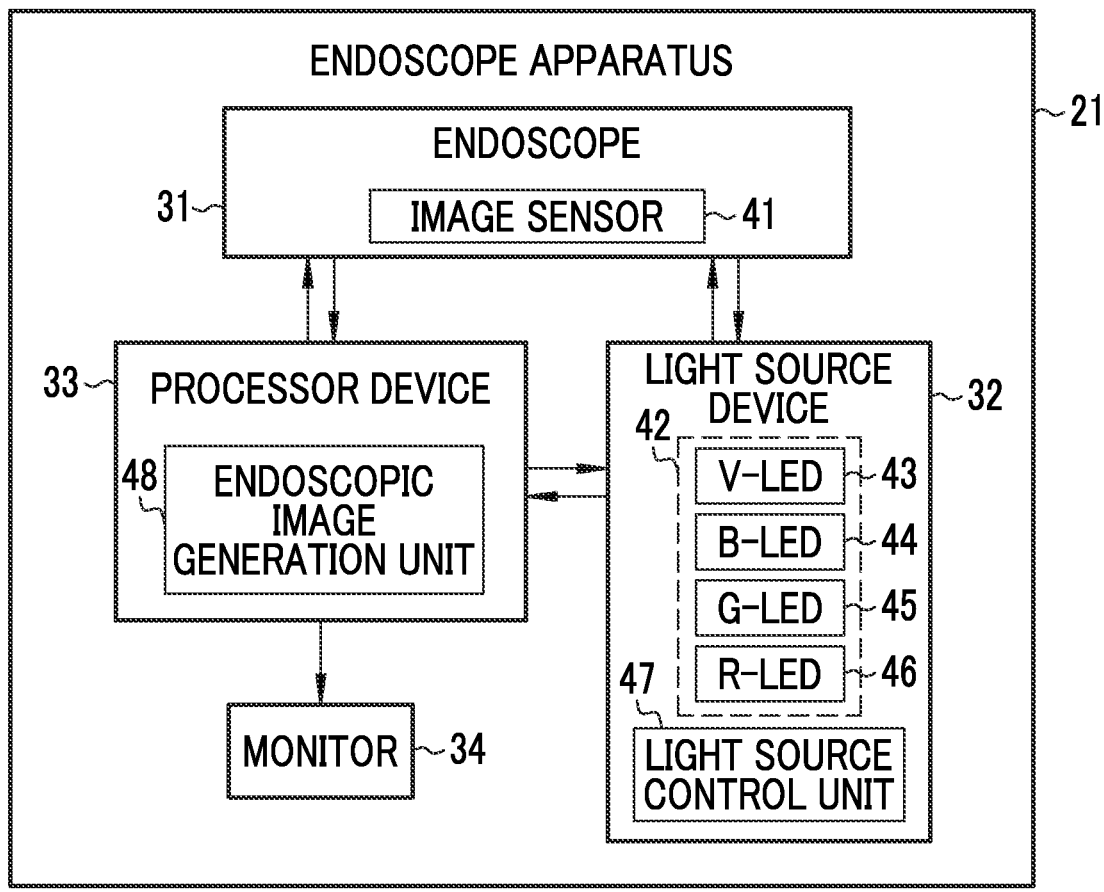
FIG. 2 is a block diagram of an endoscope apparatus.

As shown in FIG. 2, in the present embodiment, the endoscope apparatus 21 to which the medical image processing apparatus 10 is connected has an endoscope 31 that emits at least one of light in a white wavelength band or light in a specific wavelength band to image a subject, a light source device 32 that emits illumination light to the inside of the subject through the endoscope 31, a processor device 33, and a monitor 34 for displaying an endoscopic image or the like captured using the endoscope 31.

The endoscope 31 comprises an image sensor 41 that images the subject using illumination light reflected or scattered by the subject, or fluorescence emitted by the subject or a medicine or the like administered to the subject.

The image sensor 41 is, for example, a complementary metal oxide semiconductor (CMOS) color sensor (a sensor having a color filter).

The light source device 32 includes a light source unit 42 and a light source control unit 47. The light source unit 42 emits a plurality of types of illumination light having different spectra. The light source unit 42 comprises, for example, a light emitting device such as a light emitting diode (LED), a laser diode (LD), or a xenon lamp. In addition, the light source unit 42 comprises a prism, a mirror, an optical fiber, an optical filter for adjusting a wavelength band or a light amount, and the like, as necessary. In the present embodiment, the light source unit 42 comprises a V-LED 43 that emits violet light having a center wavelength of about 405 nm, a B-LED 44 that emits blue light having a center wavelength of about 450 nm, a G-LED 45 that emits green light having a center wavelength of about 540 nm, and an R-LED 46 that emits red light having a center wavelength of about 630 nm.

The light source control unit 47 controls a light emitting source included in the light source unit 42, and generates illumination light to be used by the endoscope 31 to image a subject. In a case where the light source unit 42 includes a plurality of light emitting devices, the light source control unit 47 can individually control the light emission timing and the light emission amount of each light emitting device. Therefore, the light source device 32 can supply the plurality of types of illumination light having different spectra to the endoscope 31 at any timing and any intensity. For example, in the present embodiment, the light source device 32 can emit violet light, blue light, green light, red light, or light obtained by mixing two or more of these colors at any intensity ratio in addition to white light under the control performed by the light source control unit 47, as illumination light at any timing and any intensity. In addition, the light source device 32 can emit light having a specific narrow wavelength band (a so-called narrow-band light) as illumination light due to characteristics of a light emitting device or use of an optical filter. For example, light in a shorter wavelength band than the green wavelength band, in particular, light in a blue band or a violet band of the visible range can be emitted.

The processor device 33 acquires an endoscopic image from the image sensor 41 or comprises an endoscopic image generation unit 48 that generates an endoscopic image obtained by performing image processing on the endoscopic image acquired from the image sensor 41. The image sensor 41 and the endoscopic image generation unit 48 form an "endoscopic image acquisition unit" in the endoscope apparatus 21. The endoscopic image acquisition unit acquires an endoscopic image including a subject image by imaging the subject using illumination light. The medical image processing apparatus 10 is connected to the processor device 33. The medical image acquisition unit 11 acquires the endoscopic image directly from the endoscopic image generation unit 48 of the endoscope apparatus 21.

Figure 3:
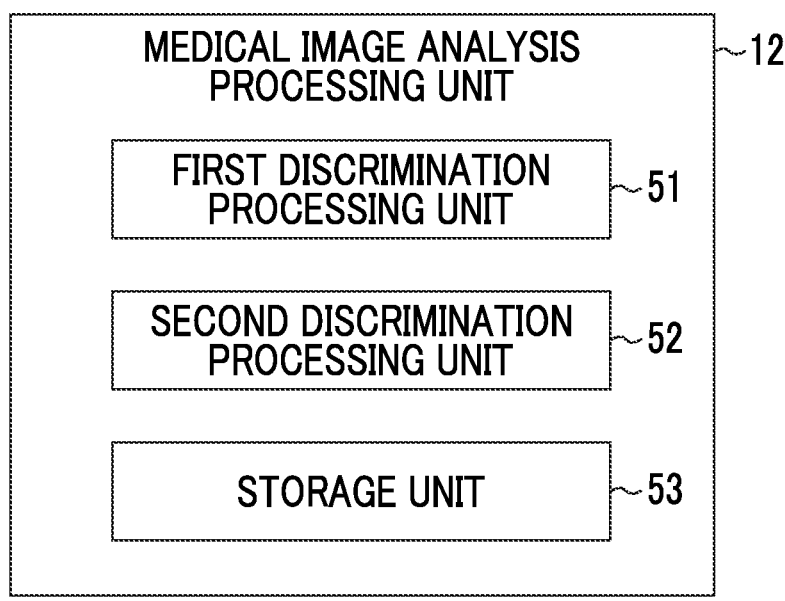
FIG. 3 is a block diagram of a medical image analysis processing unit.

The medical image analysis processing unit 12 performs an analysis process using an endoscopic image that is a medical image acquired by the medical image acquisition unit 11 (hereinafter, simply referred to as an endoscopic image). Specifically, as shown in FIG. 3, the medical image analysis processing unit includes a first discrimination processing unit 51, a second discrimination processing unit 52, and a storage unit 53.

The first discrimination processing unit 51 performs a first discrimination process of detecting a lesion and discriminating the degree of progress of the detected lesion by using a first medical image captured using first illumination light having a specific spectrum, among one or a plurality of medical images acquired by the medical image acquisition unit 11. The first medical image is, for example, a medical image captured using white light, and in the present embodiment, the first medical image is the first endoscopic image 111. For example, the first discrimination processing unit 51 calculates one or a plurality of predetermined feature amounts using the first medical image, detects a lesion or the like using the calculated feature amounts, and discriminates the degree of progress of the lesion or the like. The predetermined feature amount is a feature amount necessary for detecting a lesion or the like or discriminating the degree of progress, and differs depending on the type of a lesion or the like to be detected or a method of discriminating the degree of progress. The predetermined feature amount is a quantity related to a range of the shape, length, thickness, depth from the mucous membrane surface, density, size, distribution, and the like of a specific tissue or structure such as a blood vessel, the number of branches, complexity, disorder of regularity, or other features, for example.

In a case where the medical image acquisition unit 11 acquires an endoscopic image, the target to be detected by the first discrimination processing unit 51 as a lesion or the like is a region including a target such as one or a plurality of lesions, a region having a feature of a color or shape different from that of a surrounding tissue, a region in which a medicine is dispersed, or a region in which a treatment (a biopsy, an endoscopic mucosal resection (EMR), an endoscopic submucosal dissection (ESD), or the like) is performed. In a case where the medical image is an endoscopic image, a lesion or the like is, for example, inflammation related to an inflammatory disease, a polyp (a prominent lesion), or the like. More specifically, the polyp is a hyperplastic polyp (HP), a sessile serrated adenoma/polyp (SSA/P), an adenoma, a cancer, or the like. In addition, the region having a feature of a color or shape different from that of the surrounding tissue or the like is redness, atrophy, diverticulum, treatment scar, or the like of the subject.

In the present embodiment, the first discrimination processing unit 51 detects ulcerative colitis, which is an inflammatory bowel disease, as a lesion or the like. Then, the degree of progress is discriminated according to a so-called endoscopic finding classification. The endoscopic finding classifications of ulcerative colitis include, for example, Mayo classification, Matts classification, Ulcerative Colitis Endoscopic. Index of Severity (UCEIs) classification, and the like. In the present embodiment, among these endoscopic finding classifications, the degree of progress of ulcerative colitis in the first discrimination process is classified according to the Mayo classification. The Mayo classification includes four grades of Mayo 0 (grade 0), Mayo 1 (grade 1), Mayo 2 (grade 2), and Mayo 3 (grade 3). Mayo 0 is a grade indicating normal or inactivity (including remission). Mayo 1 is a grade indicating mild symptoms, and is generally a state where redness, unclear blood vessel image, or mild bleeding is recognized. Mayo 2 is a grade indicating moderate symptoms, and is generally a state where marked redness, loss of blood vessel image, easy bleeding, adhesion of purulent secretions, mucous membrane roughening, erosion, partial ulcers, or the like is recognized. Mayo 3 is a grade indicating severe (active stage) symptoms, and is generally a state where obvious spontaneous bleeding, edema, ulcer (including widespread ulcer), or the like is recognized. The endoscopic finding classification in a case where the cancer is a target lesion includes the narrow-band imaging international colorectal endoscopic (NICE) classification, the Japan narrow band imaging (NBI) expert team (JNET) classification, or the like.

The first discrimination processing unit 51 detects a lesion or the like for a part or all of the medical image, and discriminates the degree of progress of the lesion or the like in a case where the lesion is detected. That is, the first discrimination processing unit 51 can perform detection of a lesion or the like and discrimination of the degree of progress for each pixel, for each small region in a case of dividing an endoscopic image into small regions, or for the entire endoscopic image. In the present embodiment, the first discrimination processing unit 51 detects a lesion or the like and discriminates the degree of progress for each small region including a predetermined number of pixels. Therefore, the first discrimination processing unit 51 can detect a lesion or the like at one or a plurality of locations in the medical image. In addition, the first discrimination processing unit 51 can include, in a determination result, at least the presence or absence of a lesion or the like and the degree of progress, or the "probability" indicating the likelihood of the result of detection of a lesion or the like and discrimination of the degree of progress.

The second discrimination processing unit 52 performs a second discrimination process of discriminating the degree of progress of the detected lesion or the like by using a second medical image captured using second illumination light having a spectrum different from the first illumination light, among the medical images. The second medical image is, for example, a medical image captured using the second illumination light having a narrower wavelength band than the first illumination light, and in the present embodiment, the second medical image is the second endoscopic image 121. The first discrimination process is a somewhat general-purpose process of detecting a lesion or the like and roughly discriminating the degree of progress of the detected lesion or the like, whereas the second discrimination process is a process of discriminating the degree of progress in more detail than the first discrimination process by matching the characteristics of a lesion or the like on the assumption that there is the lesion or the like. For example, the second discrimination processing unit 52 calculates one or a plurality of predetermined feature amounts using the second medical image, and discriminates the degree of progress of a lesion or the like using the calculated feature amounts. The predetermined feature amount calculated by the second discrimination processing unit 52 is a feature amount necessary for discriminating the degree of progress of a lesion or the like in detail, and differs depending on the type of a lesion or the like to be detected or a method of discriminating the degree of progress. The second discrimination processing unit 52 can calculate any feature amount necessary similarly to the predetermined feature amount calculated by the first discrimination processing unit 51.

The second discrimination processing unit 52 may always perform the second discrimination process, or may perform the second discrimination process as necessary. For example, the second discrimination processing unit 52 may perform the second discrimination process in a case where the type of the lesion or the like detected in the first discrimination process is a specific type, or in a case where the lesion or the like detected in the first discrimination process indicates a specific degree of progress. In a case where the second discrimination processing unit 52 performs the second discrimination process, the result of the second discrimination process is output as the final discrimination result, and in a case where the second discrimination processing unit does not perform the second discrimination process, the result of the first discrimination process is output as the final discrimination result. Specifically, in a case where the first discrimination processing unit 51 detects ulcerative colitis as the lesion or the like and discriminates the grade of the endoscopic finding classification as the degree of progress of the ulcerative colitis, the second discrimination processing unit 52 performs the second discrimination process in a case where the grade of the ulcerative colitis is a specific grade. Then, the second discrimination processing unit 52 outputs a discrimination result obtained by further subdividing the grade of the endoscopic finding classification.

In the present embodiment, the second discrimination processing unit 52 performs discrimination that further subdivides the degree of progress classified based on the endoscopic finding classification in the first discrimination process. Specifically, as shown in FIG. 4, the second discrimination processing unit 52 performs the second discrimination process in a case where the degree of progress of ulcerative colitis is Mayo 0 or Mayo 1, and does not perform the second discrimination process in a case where the degree of progress of ulcerative colitis is Mayo 2 or Mayo 3. In a case where the ulcerative colitis is Mayo 0 among the four grades in the Mayo classification, the second discrimination processing unit 52 further subdivides Mayo 0 into three grades of Mayo 0-I, Mayo 0-II, and Mayo 0-III to discriminate the degree of progress. Mayo 0-I indicates the most distant from Mayo 1 in Mayo 0 and almost certainly normal or inactive. Mayo 0-III indicates the degree of progress close to Mayo 1 in Mayo 0. Mayo 0-II indicates that the degree of progress is intermediate between Mayo 0-I and Mayo 0-III. In addition, in a case where the degree of progress of the ulcerative colitis is Mayo 1, the second discrimination processing unit 52 further subdivides Mayo 1 into three stages of Mayo 1-I, Mayo 1-II, and Mayo 1-III to discriminate the degree of progress. Mayo 1-I indicates that the degree of progress is close to Mayo 0 in Mayo 1, and Mayo 1-III indicates that the degree of progress is close to Mayo 2 in Mayo 1. Mayo 1-II indicates that the degree of progress is intermediate between Mayo 1-I and Mayo 1-III.

The storage unit 53 stores a combination of first illumination light for acquiring a first medical image used for the first discrimination process and second illumination light for acquiring a second medical image used for the second discrimination process in advance, for each type or degree of progress of a lesion or the like to be detected. For this reason, in a case where the type of a lesion or the like to be detected and discriminated is determined by the setting, the first discrimination processing unit 51 uses the first medical image captured using the first illumination light for the first discrimination process according to the combination stored in the storage unit 53. Similarly, in a case where the type of a lesion or the like to be detected and discriminated is determined by the setting, the second discrimination processing unit 52 uses the second medical image captured using the second illumination light for the second discrimination process according to the combination stored in the storage unit 53. The combination of the first illumination light and the second illumination light stored in the storage unit 53 is determined in advance according to the type of the lesion or the like detected in the first discrimination process or the degree of progress of the lesion or the like detected in the first discrimination process.

Note that the medical image acquisition unit 11 can acquire in advance a medical image that may be requested by the first discrimination processing unit 51 and the second discrimination processing unit 52. In a case where the medical image requested by the first discrimination processing unit 51 or the second discrimination processing unit 52 has not been acquired, the medical image acquisition unit 11 acquires a medical image used for the second discrimination process according to the request of the first discrimination processing unit 51 or the second discrimination processing unit 52.

In addition, the first discrimination processing unit 51 and the second discrimination processing unit 52 each perform a discrimination process while the display control unit 15 is displaying the endoscopic image 101 for display, which is a medical image for display, on the display unit 13. Here, the display control unit 15 may update the endoscopic image 101 for display that is displayed on the display unit 13 while the first discrimination process or the second discrimination process is performed. That is, the expression " . . . each perform a discrimination process while the display control unit 15 is displaying the endoscopic image 101 for display, which is a medical image for display, on the display unit 13" means that the first discrimination process and the second discrimination process are executed in the background of the display control for displaying the endoscopic image 101 for display on the display unit 13.

The display unit 13 is a display for displaying a medical image acquired by the medical image acquisition unit 11, a detection result of a lesion or the like, and a discrimination result of the lesion or the like. A monitor or a display included in a device or the like to which the medical image processing apparatus 10 is connected can be shared and used as the display unit 13 of the medical image processing apparatus 10.

The display control unit 15 controls a display mode of the medical image, the detection result of the lesion or the like on the display unit 13, and the discrimination result of the lesion or the like. In the present embodiment, the display control unit 15 displays at least the discrimination result of the second discrimination processing unit 52 using the display unit 13 or the like. Specifically, the position of the lesion or the like detected by the first discrimination processing unit 51 is displayed so as to be superimposed on the endoscopic image 101 for display, and a message indicating the degree of progress of the lesion or the like, which is a determination result by the second discrimination processing unit 52, or the like is displayed on the display unit 13. Depending on the setting, the display control unit 15 can show the position of the detected lesion or the like and the discrimination result of the second discrimination processing unit 52 by any other method such as sound (including voice), light (such as partial blinking of the endoscopic image 101 for display), display of coordinates, and the like.

The input receiving unit 16 receives inputs from a mouse, a keyboard, and other operation devices connected to the medical image processing apparatus 10. An operation of each unit of the medical image processing apparatus 10 can be controlled using the operation devices.

The overall control unit 17 controls the overall operation of each unit of the medical image processing apparatus 10. In a case where the input receiving unit 16 receives an operation input using an operation device, the overall control unit 17 controls each unit of the medical image processing apparatus 10 according to the operation input.

The storage unit 18 stores the detection result of the lesion or the like, the discrimination result of the degree of progress, or both of them, as necessary in a storage device (not shown) such as a memory included in the medical image processing apparatus 10 or a storage device (not shown)

included in a medical apparatus such as the endoscope apparatus 21 or the PACS 22.

Figure 5:
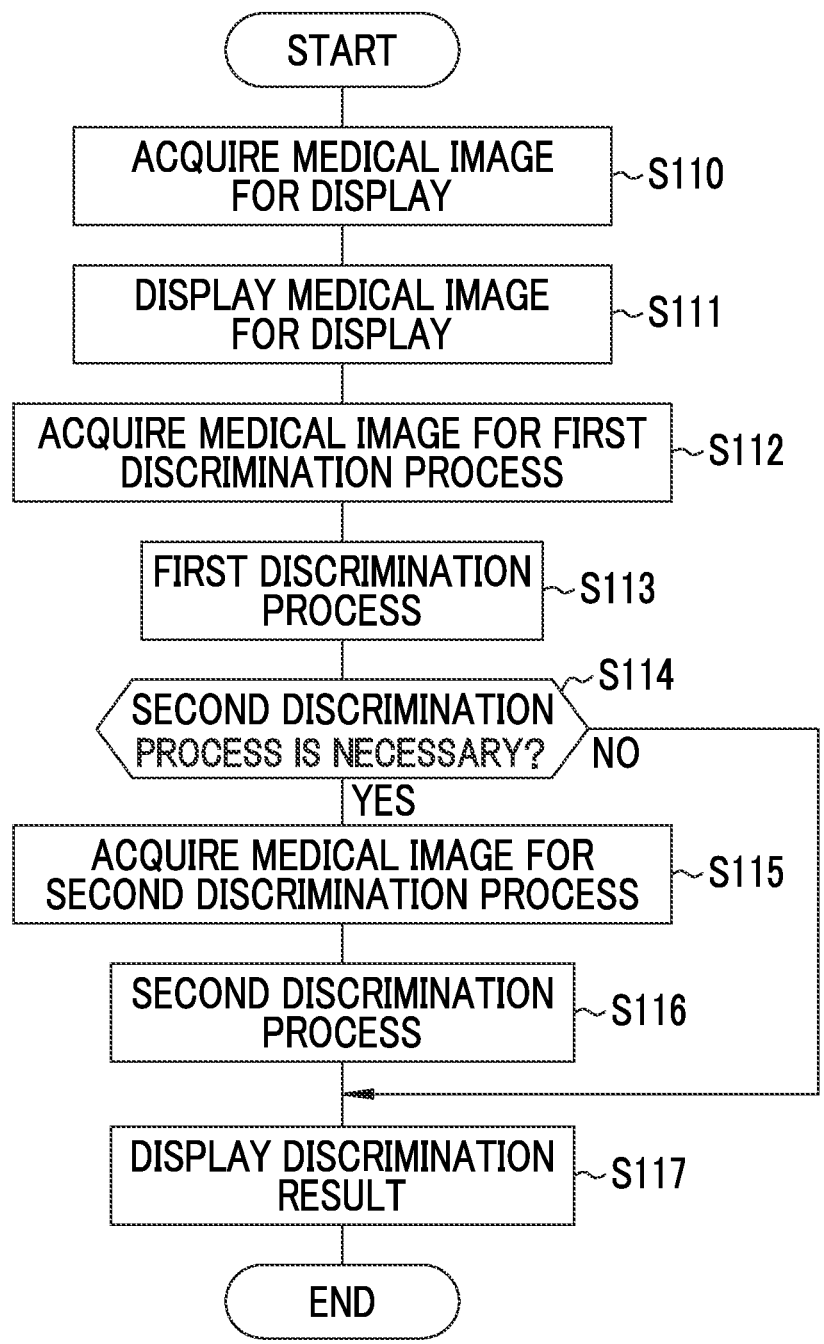
FIG. 5 is a flowchart showing an operation of the medical image processing apparatus.
Figure 6:
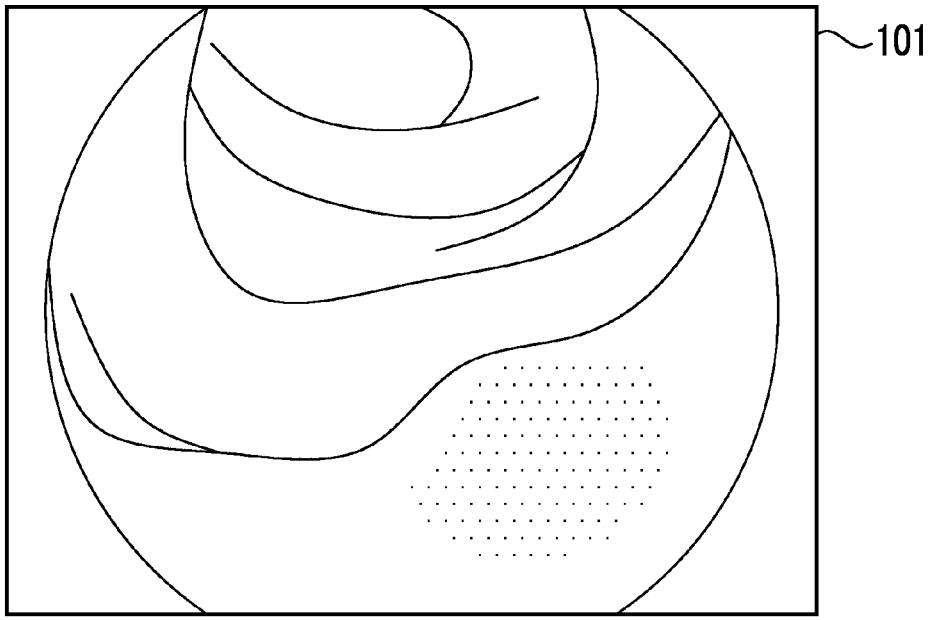
FIG. 6 is a medical image for display.

Hereinafter, a flow of the operation of the medical image processing apparatus 10 will be described. As shown in FIG. 5, the medical image acquisition unit 11 acquires a plurality of endoscopic images 101 for display automatically or by manual selection (step S110), and the display control unit 15 sequentially displays the endoscopic images 101 for display that is acquired by the medical image acquisition unit 11 on the display unit 13 (step S111). In the present embodiment, for example, the endoscopic image 101 for display shown in FIG. 6 is acquired and displayed.

Figure 7:
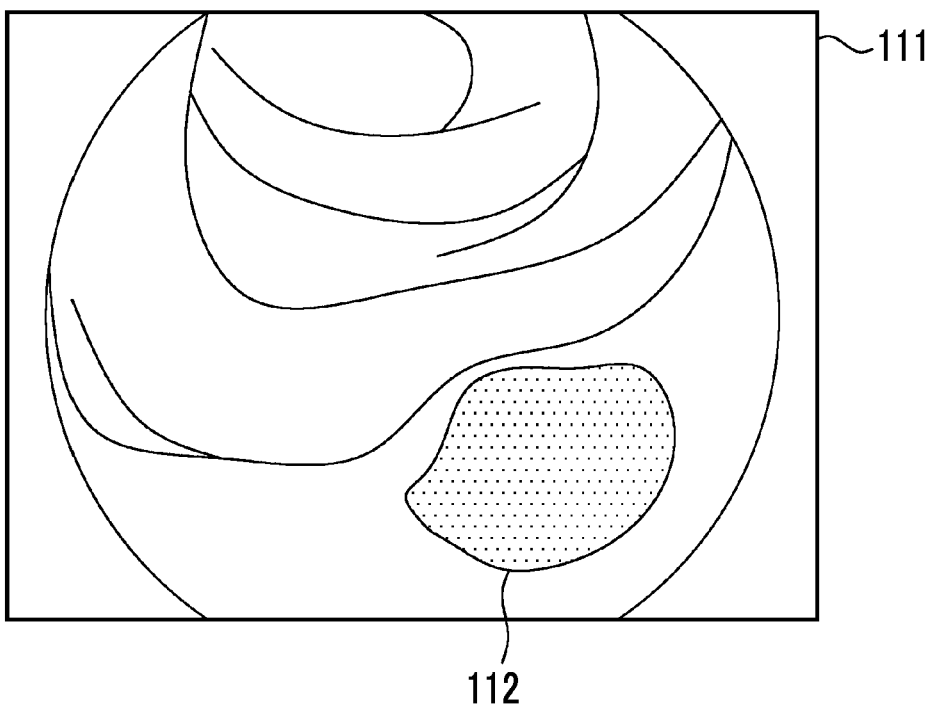
FIG. 7 is an endoscopic image for the first discrimination process.

Meanwhile, in the background, the medical image acquisition unit 11 acquires a first medical image that is a medical image for the first discrimination process (step S112). In the present embodiment, since ulcerative colitis is a detection target, as shown in FIG. 7, the medical image acquisition unit 11 acquires the first endoscopic image 111 captured using white light (first illumination light) as the first medical image.

In a case where the medical image acquisition unit 11 acquires the first endoscopic image 111 (after acquiring), the first discrimination processing unit 51 performs the first discrimination process using the first endoscopic image 111 (step S113). For example, the first discrimination processing unit 51 detects, from the first endoscopic image 111, a region 112 having inflammation caused by ulcerative colitis (hereinafter, referred to as an inflammatory region). Then, the degree of progress of ulcerative colitis is discriminated using the feature amount of the inflammatory region 112. In the present embodiment, it is assumed that the degree of progress of ulcerative colitis is Mayo 1 grade in the Mayo classification.

Figure 8:
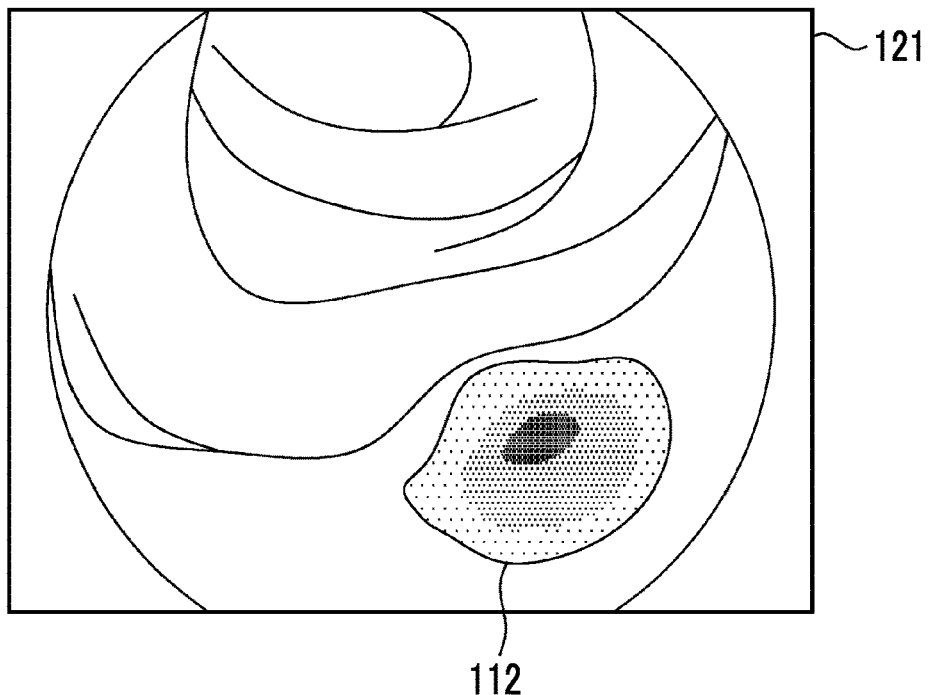
FIG. 8 is an endoscopic image for the second discrimination process.

In a case where the first discrimination processing unit 51 completes the detection of the lesion or the like and the discrimination of the degree of progress of the lesion or the like (after completion), the second discrimination processing unit 52 determines the necessity of the second discrimination process (step S114). Then, in a case where the second discrimination process is necessary (step S114: YES), the medical image acquisition unit 11 acquires a second medical image that is a medical image for the second discrimination process (step S115). In the present embodiment, since ulcerative colitis is a detection target, as shown in FIG. 8, the medical image acquisition unit 11 acquires the second endoscopic image 121 captured using illumination light (second illumination light) with more specific blue or specific violet than white light, as the second medical image. Since the second endoscopic image 121 is captured using illumination light with more specific blue or specific violet than white light, the tissue or structure of the inflammatory region 112 can be observed in more detail than the first endoscopic image 111.

In a case where the medical image acquisition unit 11 acquires the second endoscopic image 121 for the second discrimination process (after acquiring), the second discrimination processing unit 52 performs the second discrimination process using the second endoscopic image 121 (step S116). Specifically, the second discrimination processing unit 52 calculates a predetermined feature amount (disorder of regularity or the like) for the inflammatory region 112 where the tissue or structure of the inflammatory region 112 is clear, and discriminates the degree of progress of further subdividing the Mayo classification using the calculated predetermined feature amount. In the present embodiment, it is assumed that the discrimination result of ulcerative colitis in the second discrimination process is Mayo 1-I.

Figure 9:
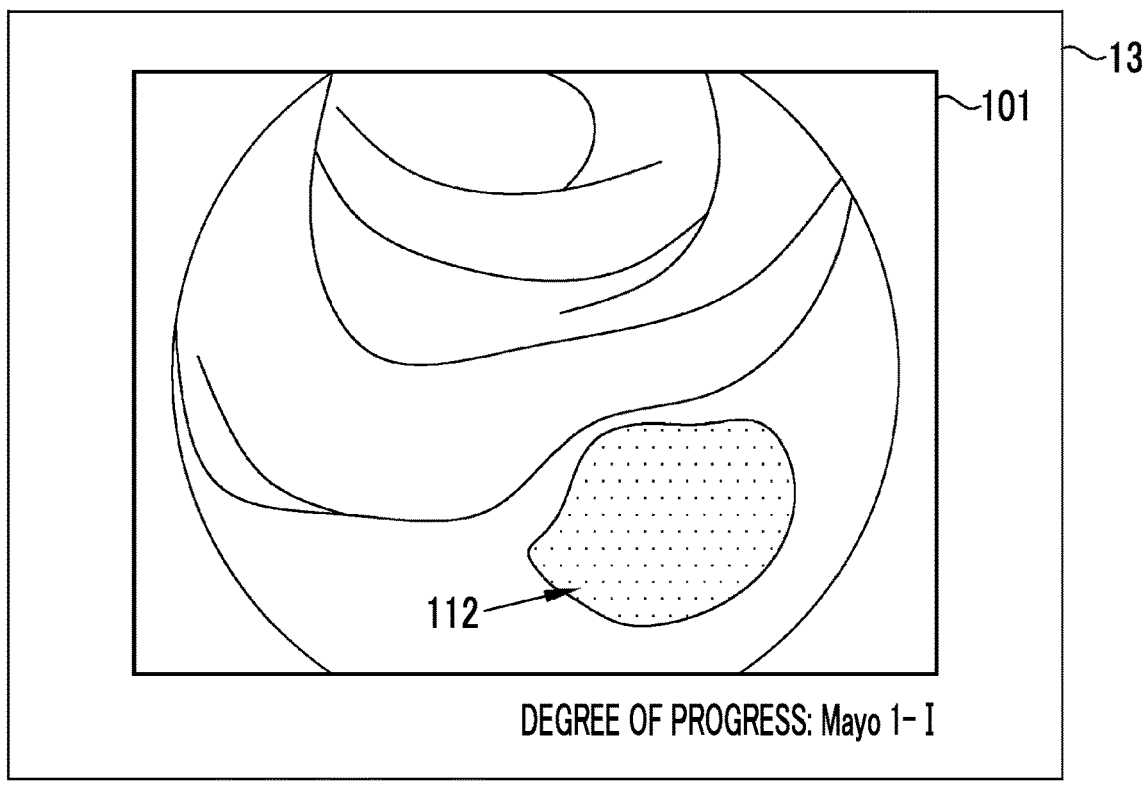
FIG. 9 is a display example of a discrimination result.

As described above, in a case where the second discrimination process is completed (after completion), for example, as shown in FIG. 9, the display control unit 15 indicates the location of the inflammatory region 112 by showing an outline in the endoscopic image 101 for display, and indicates the grade of the subdivided Mayo classification that is the discrimination result of the second discrimination process (step S117).

As described above, as a first stage, the medical image processing apparatus 10 detects a lesion or the like and discriminates the degree of progress of the lesion or the like according to the classification. This is sufficient as information presented by the medical apparatus to support diagnosis and the like. However, as a second stage, the medical image processing apparatus 10 further subdivides general classifications and the like, discriminates the degree of progress of the detected lesion or the like, and presents the result to a doctor or the like. The doctor or the like can easily perform a discrimination diagnosis by examining the discrimination results that are further subdivided than before, which are presented by the medical image processing apparatus 10. That is, the medical image processing apparatus 10 can provide more detailed information regarding a lesion or the like than before, and can more effectively support diagnosis and the like.

In particular, regarding ulcerative colitis, in a case where the degree of progress is between Mayo 0 and Mayo 1, characteristics such as inflammation are relatively small, so that discrimination diagnosis is not easy, and accurately discriminating the degree of progress between Mayo 0 and Mayo 1 is particularly important in the treatment of ulcerative colitis and the like. This is because, for example, even in a case of the degree of progress of Mayo 1, handling may be different between a state close to Mayo 2 and a state close to Mayo 0. Therefore, as described above, the degree of progress of Mayo 0 or Mayo 1 is further subdivided and discriminated, and the result is presented, so that the medical image processing apparatus 10 can particularly effectively support diagnosis and the like of ulcerative colitis.

In the first embodiment described above, ulcerative colitis is a detection target, and the degree of progress is discriminated according to the Mayo classification, but the case of discriminating the degree of progress of ulcerative colitis using an endoscopic finding classification other than the Mayo classification is also the same as in the first embodiment. For example, grade 1, grade 2, grade 3, and grade 4 of the Matts classification generally correspond to grade 0, grade 2, grade 3, and grade 4 of the Mayo classification, respectively. For this reason, in a case where ulcerative colitis is a detection target and the degree of progress is discriminated according to the Matts classification, the second discrimination processing unit 52 does not perform the second discrimination process in a case where the degree of progress of the ulcerative colitis is grade 3 or more, and performs the second discrimination process in a case where the degree of progress of the ulcerative colitis is grade 1 or grade 2.

In the first embodiment described above, the second discrimination processing unit 52 discriminates the degree of progress of the ulcerative colitis by further subdividing Mayo 1 and Mayo 0 into three grades in the second discrimination process, but which grade is further subdivided in the second discrimination process is optional. In addition, the number of stages to be subdivided is also optional. The same applies to a case where a lesion other than ulcerative colitis is detected or a case where the first discrimination process is performed according to a classification other than the Mayo classification.

In the first embodiment described above, the first discrimination processing unit 51 detects ulcerative colitis, which is an inflammatory bowel disease, as a lesion or the like, but the first discrimination processing unit 51 can detect a cancer or a disease state that may develop into a cancer (including benign polyps that are unlikely to develop into a cancer but need to be discriminated, in addition to an adenoma or the like, hereinafter, referred to as a cancer or the like). In a case where the first discrimination processing unit 51 detects a cancer or the like as a lesion or the like, the second discrimination processing unit 52 does not perform the second discrimination process in a case where the lesion or the like detected in the first discrimination process is not a cancer, and performs the second discrimination process in a case where the cancer is detected in the first discrimination process. In addition, in a case where a cancer or the like is a detection target, the second discrimination processing unit 52 can output information related to prediction of a treatment effect as a discrimination result instead of further subdividing and discriminating the degree of progress than before. The information related to prediction of the treatment effect is, for example, information including the content such as whether or not a specific treatment medicine or treatment method is effective for the detected cancer or the like, or how effective the specific treatment medicine or treatment method is for the detected cancer or the like.

In the first embodiment described above, the first discrimination process and the second discrimination process are performed by calculating a predetermined feature amount, but the first discrimination processing unit 51 or the second discrimination processing unit 52 can detect the lesion or the like or discriminate the degree of progress of the lesion or the like by using, for example, texture analysis or pattern matching using a regular shape, instead of using the feature amount.

The first discrimination processing unit 51, the second discrimination processing unit 52, and the storage unit 53 in the first embodiment can be configured using a so-called artificial intelligence (AI) program learned by machine learning, deep learning, or the like.

Second Embodiment

Figure 10:
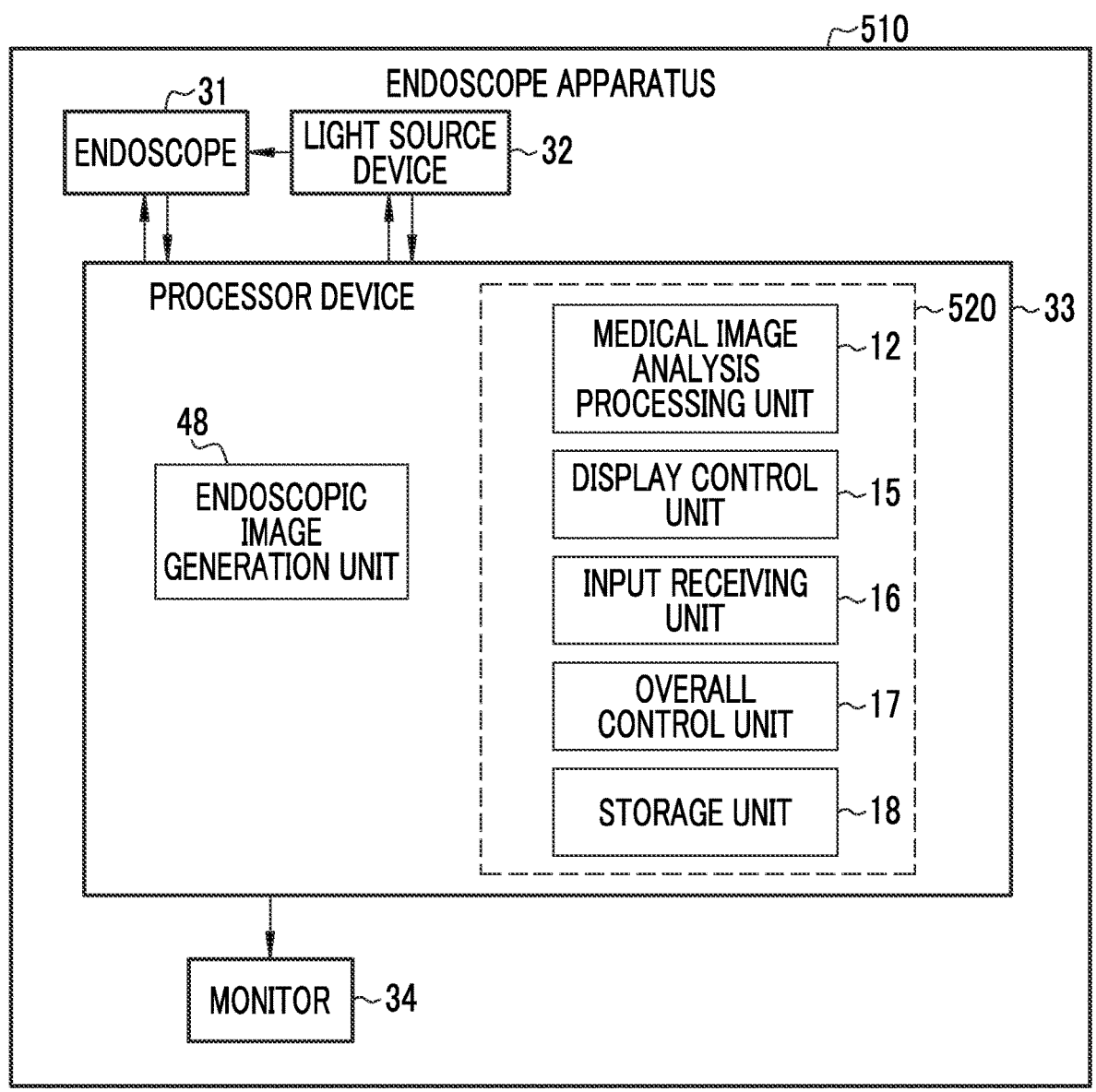
FIG. 10 is a block diagram of an endoscope apparatus including a medical image processing apparatus.

In the first embodiment described above, the medical image processing apparatus 10 and the endoscope apparatus 21 are separate apparatuses. However, the endoscope apparatus 21 can include the medical image processing apparatus 10. In this case, as an endoscope apparatus 510 shown in FIG. 10, each unit 520 forming the medical image processing apparatus 10 is provided in the processor device 33. Here, the display unit 13 can share the monitor 34 of the endoscope apparatus 21. In addition, the medical image acquisition unit 11 corresponds to an "endoscopic image acquisition unit" formed by the image sensor 41 and the endoscopic image generation unit 48. For this reason, it is sufficient to provide the processor device 33 with each unit other than the medical image acquisition unit 11 and the display unit 13. The configuration of each of other units is the same as in the first embodiment. In addition, a new endoscope apparatus can be configured by all of the medical image processing apparatuses 10 of each embodiment described above and other modification examples and the endoscope apparatus 21 shown in FIG. 2.

The endoscope apparatus 510 including the medical image processing apparatus 10 is an apparatus that basically observes a subject in real time. For this reason, the endoscope apparatus 510 can execute acquisition of the endoscopic image that is a medical image, the first discrimination process, the second discrimination process, the display process of the discrimination result, and the like in real time while capturing the endoscopic image or at any timing due to the operation of various operation units or the like.

Figure 11:
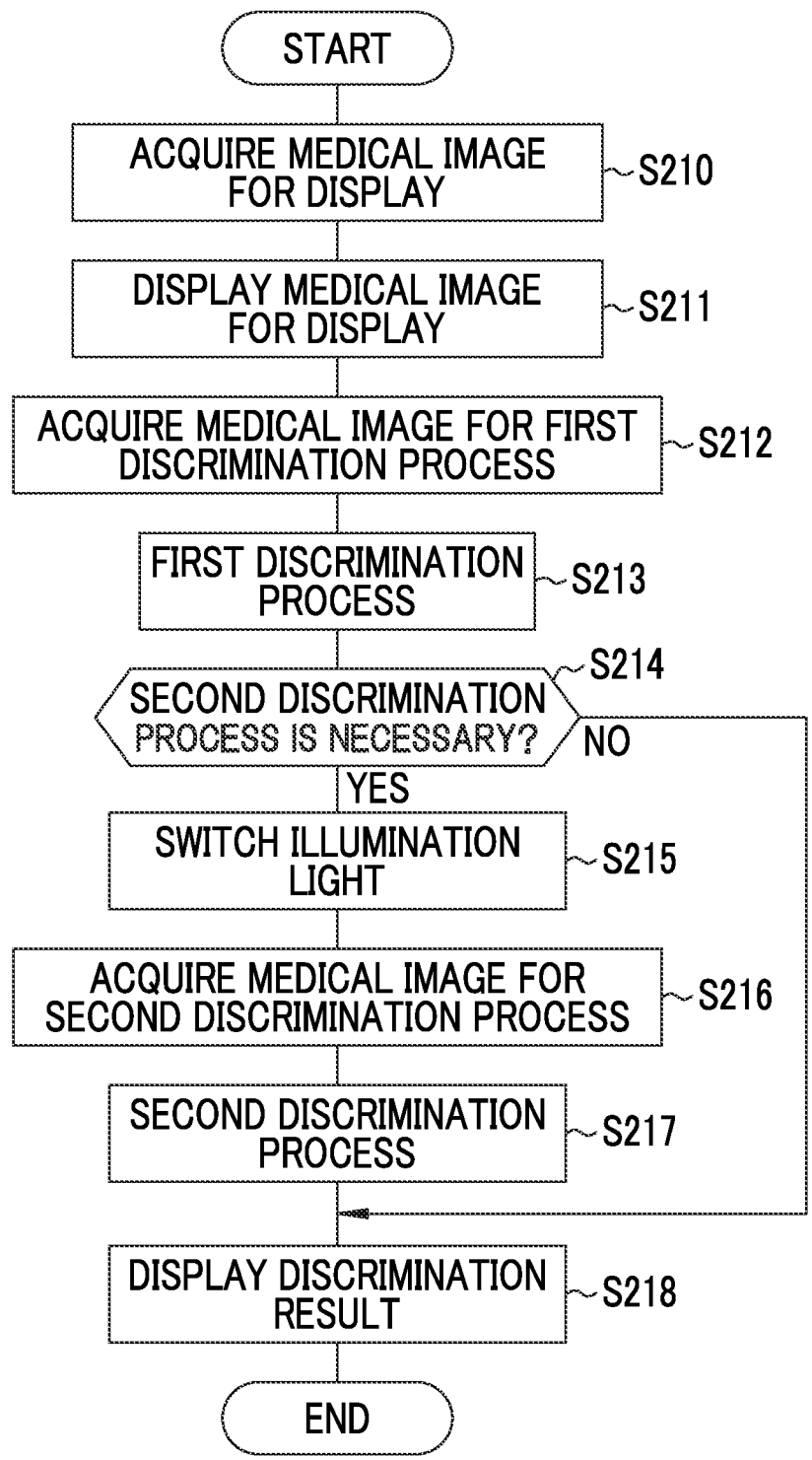
FIG. 11 is a flowchart in a case of detecting a lesion or the like and discriminating a degree of progress in real time in the endoscope apparatus.

Hereinafter, an operation flow in the case where the endoscope apparatus 510 including the medical image processing apparatus 10 detects a lesion or the like and discriminates the degree of progress in real time will be described. As shown in FIG. 11, the endoscope apparatus 510 sequentially images a subject using, for example, white light, acquires an endoscopic image 101 for display (step S210), and displays the acquired endoscopic image 101 for display on the monitor 34 (step S211). The endoscope apparatus 510 repeatedly executes these steps at, for example, a predetermined frame rate at all times. For this reason, a doctor or the like can observe the subject in real time.

In addition, the overall control unit 17 intermittently interrupts the imaging for the first discrimination process at a predetermined timing that does not hinder the continuous display of the endoscopic images 101 for display during imaging of the series of endoscopic images 101 for display. Thereby, the endoscopic image acquisition unit acquires the first endoscopic image 111 that is a medical image for the first discrimination process (step S212). Here, in a case where ulcerative colitis is a detection target, since the first endoscopic image 111 for the first discrimination process is captured using white light in the same manner as the endoscopic image 101 for display, the step S212 is omitted, and the endoscopic image 101 for display can be used for the first discrimination process.

The first discrimination processing unit 51 performs the first discrimination process using the first endoscopic image 111 acquired in real time as described above (step S213). Thereby, the first discrimination processing unit 51 detects an inflammatory region 112 caused by ulcerative colitis and discriminates the degree of progress of ulcerative colitis according to, for example, Mayo classification. These are the same as in the first embodiment.

Thereafter, the second discrimination processing unit 52 determines the necessity of the second discrimination process (step S214). In a case where the second discrimination process is necessary (step S214: YES), the overall control unit 17 intermittently interrupts the imaging for the second discrimination process at a predetermined timing that does not hinder the continuous display of the endoscopic images 101 for display during imaging of the series of endoscopic images 101 for display. That is, the light source control unit 47 switches the illumination light to second illumination light having a different spectrum from the first illumination light in accordance with the type or degree of progress of the lesion, and the image sensor 41 images a subject using the second illumination light. Thereby, the endoscopic image acquisition unit acquires the second endoscopic image 121 that is a medical image for the second discrimination process (step S216).

In a case where detection of a lesion or the like and discrimination of the degree of progress are performed in real time, the storage unit 53 stores a combination (each spectrum of the first illumination light and the second illumination light, a light amount ratio of a light emitting source for realizing the first illumination light and the second illumination light having a specific spectrum, or the like) of the first illumination light used for the capturing of the first medical image and the second illumination light used for the capturing of the second medical image in advance, for each type or degree of progress of the lesion or the like to be detected. The light source control unit 47 controls the light source unit 42 with reference to the combination stored in the storage unit 53. For this reason, the light source unit 42 emits an appropriate first illumination light at the time of imaging for the first discrimination process, and emits an appropriate second illumination light at the time of imaging for the second discrimination process.

In a case where the medical image acquisition unit 11 acquires the second endoscopic image 121 for the second discrimination process (after acquiring), the second discrimination processing unit 52 executes the second discrimination process in real time using the second endoscopic image 121 in the background of the display control (step S117). In a case where the second discrimination process is completed (after completion), the display control unit 15 indicates the location of the inflammatory region 112 by showing an outline in the endoscopic image 101 for display, and indicates the grade of the subdivided Mayo classification that is the discrimination result of the second discrimination process (step S118).

As described above, the endoscope apparatus 510 including the medical image processing apparatus 10 can perform the first discrimination process, the second discrimination process, and the like in real time, and support diagnosis and the like in real time.

Figure 12:
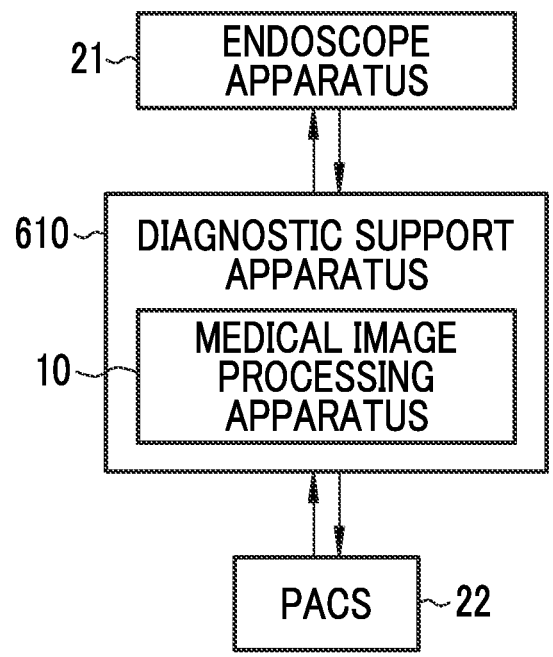
FIG. 12 is a diagnostic support apparatus including the medical image processing apparatus.
Figure 13:
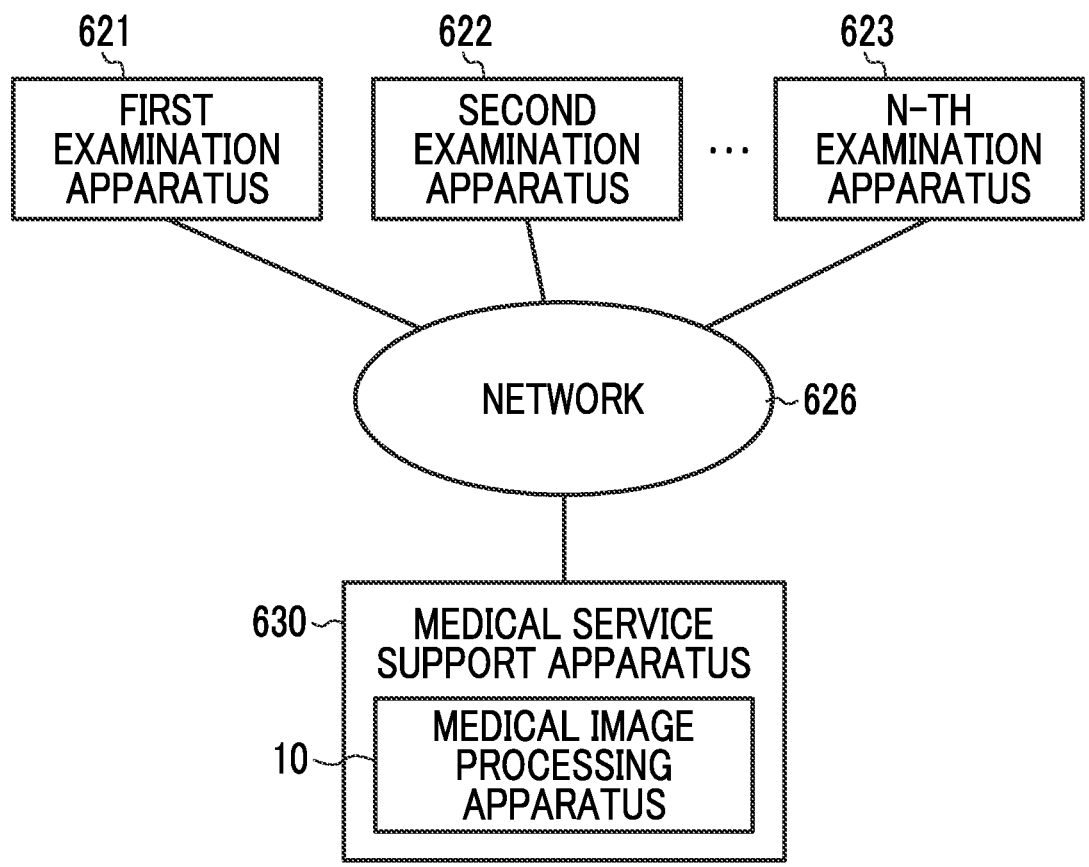
FIG. 13 is a medical service support apparatus including the medical image processing apparatus.

In the second embodiment described above, the endoscope apparatus 510 includes the medical image processing apparatus 10. However, as shown in FIG. 12, a diagnostic support apparatus 610 used in combination with the endoscope apparatus 21 and other modalities can include the medical image processing apparatuses 10 of the above embodiments and other modification examples. In addition, as shown in FIG. 13, for example, a medical service support apparatus 630 connected to various examination apparatuses including the endoscope apparatus 21, such as a first examination apparatus 621, a second examination apparatus 622, . . . , and an N-th examination apparatus 623, through a certain network 626 can include the medical image processing apparatuses 10 of the above embodiment and other modification examples.

In addition to this, the medical image processing apparatus 10, various apparatuses including the medical image processing apparatus 10, and various apparatuses or systems having a function of the medical image processing apparatus 10 can be used by making the following various changes or the like.

As the medical image, it is possible to use a normal light image obtained by emitting light in a white band or light in a plurality of wavelength bands as light in the white band.

In a case where an image obtained by emitting light in a specific wavelength band is used as the medical image, a band narrower than the white wavelength band can be used as the specific wavelength band.

The specific wavelength band is, for example, a blue band or a green band of a visible range.

In a case where the specific wavelength band is the blue band or the green band of a visible range, it is preferable that the specific wavelength band includes a wavelength band of 390 nm to 450 nm or a wavelength band of 530 nm to 550 nm and that light in the specific wavelength band has a peak wavelength within the wavelength band of 390 nm to 450 nm or the wavelength band of 530 nm to 550 nm.

The specific wavelength band is, for example, a red band of a visible range.

In a case where the specific wavelength band is the red band of a visible range, it is preferable that the specific wavelength band includes a wavelength band of 585 nm to 615 nm or a wavelength band of 610 nm to 730 nm and that light in the specific wavelength band has a peak wavelength within the wavelength band of 585 nm to 615 nm or the wavelength band of 610 nm to 730 nm.

The specific wavelength band can include, for example, a wavelength band in which light absorption coefficients of oxygenated hemoglobin and reduced hemoglobin are different, and light in the specific wavelength band can have a peak wavelength in the wavelength band in which light absorption coefficients of oxygenated hemoglobin and reduced hemoglobin are different.

In a case where the specific wavelength band includes a wavelength band in which the light absorption coefficients of oxygenated hemoglobin and reduced hemoglobin are different and light in the specific wavelength band has a peak wavelength in the wavelength band in which the light absorption coefficients of oxygenated hemoglobin and reduced hemoglobin are different, it is preferable that the specific wavelength band includes a wavelength band of 400±10 nm, 440±10 nm, 470±10 nm, or 600 nm to 750 nm and that light in the specific wavelength band has a peak wavelength within the wavelength band of 400±10 nm, 440±10 nm, 470±10 nm, or 600 nm to 750 nm.

In a case where the medical image is an in-vivo image of the living body, the in-vivo image can have information on fluorescence emitted from the fluorescent material in the living body.

In addition, as the fluorescence, fluorescence obtained by emitting excitation light having a peak wavelength of 390 nm to 470 nm to the inside of the living body can be used.

In a case where the medical image is an in-vivo image of the living body, the wavelength band of infrared light can be used as the specific wavelength band described above.

In a case where the medical image is an in-vivo image of the living body and the wavelength band of infrared light is used as the specific wavelength band described above, it is preferable that the specific wavelength band includes a wavelength band of 790 nm to 820 nm or 905 nm to 970 nm and that light in the specific wavelength band has a peak wavelength within the wavelength band of 790 nm to 820 nm or 905 nm to 970 nm.

The medical image acquisition unit 11 can have a special light image acquisition section that acquires a special light image having a signal in a specific wavelength band on the basis of a normal light image obtained by emitting light in a white band or light in a plurality of wavelength bands as light in the white band. In this case, the special light image can be used as the medical image.

The signal in a specific wavelength band can be obtained by calculation based on the color information of RGB or CMY included in the normal light image.

It is possible to comprise a feature amount image generation unit that generates a feature amount image by calculation based on at least one of the normal light image obtained by emitting light in a white band or light in a plurality of wavelength bands as light in the white band or the special light image obtained by emitting light in a specific wavelength band. In this case, the feature amount image can be used as the medical image.

In the endoscope apparatus 21, a capsule endoscope can be used as the endoscope 31. In this case, the light source device 32 and a part of the processor device 33 can be mounted in the capsule endoscope.

In the above embodiments and modification examples, hardware structures of processing units for executing various kinds of processing, such as the medical image acquisition unit 11, the medical image analysis processing unit 12 (each unit forming the medical image analysis processing unit 12), the display control unit 15, the input receiving unit 16, the overall control unit 17, and the endoscopic image generation unit 48 of the endoscope apparatus 21, are various processors shown below. The various processors include a central processing unit (CPU) that is a general-purpose processor that functions as various processing units by executing software (program), a programmable logic device (PLD) that is a processor whose circuit configuration can be changed after manufacture, such as field programmable gate array (FPGA), a dedicated electrical circuit that is a processor having a dedicated circuit configuration for executing various types of processing, and the like.

One processing unit may be configured by one of various processors, or may be configured by a combination of two or more processors of the same type or different types (for example, a combination of a plurality of FPGAs or a combination of a CPU and an FPGA). In addition, a plurality of processing units may be configured by one processor. As an example of configuring a plurality of processing units by one processor, first, as represented by a computer, such as a client or a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as a hardware structure.

More specifically, the hardware structure of these various processors is an electrical circuit (circuitry) in the form of a combination of circuit elements, such as semiconductor elements.

EXPLANATION OF REFERENCES

10: medical image processing apparatus
11: medical image acquisition unit
12: medical image analysis processing unit
13: display unit
15: display control unit
16: input receiving unit
17: overall control unit
18: storage unit
21, 510: endoscope apparatus
22: PACS
31: endoscope
32: light source device
33: processor device
34: monitor
41: image sensor
42: light source unit
43: V-LED
44: B-LED
45: G-LED
46: R-LED
47: light source control unit
48: endoscopic image generation unit
51: first discrimination processing unit
52: second discrimination processing unit
53: storage unit
101: endoscopic image for display
111: first endoscopic image
112: inflammatory region
121: second endoscopic image
520: each unit forming medical image processing apparatus
610: diagnostic support apparatus
621: first examination apparatus
622: second examination apparatus
623: N-th examination apparatus
626: network
630: medical service support apparatus
S110 to S218: steps of operation

What is claimed is:

1. A medical image processing apparatus comprising:
one or more processors configured to:
   acquire a plurality of medical images captured by alternately switching illumination light emitted from an endoscope to first illumination light and second illumination light having a spectrum different from the first illumination light;
   perform a detection process of detecting a lesion by using a first medical image captured using the first illumination light, among the medical images;
   perform a discrimination process of discriminating a type or a degree of progress of the lesion by using a second medical image captured using the second illumination light, among the medical images;
   superimpose information indicating a position of the lesion detected in the detection process on an image captured using the first illumination light among the plurality of medical images, and display the superimposed information and the image on a monitor; and
   display a discrimination result of the lesion discriminated in the discrimination process on the monitor,
wherein the first medical image is the medical image captured using white light,
wherein the second medical image is the medical image captured using the second illumination light having a narrower wavelength band than the first illumination light.

2. The medical image processing apparatus according to claim 1,
wherein, in a case where the one or more processors discriminate a grade of an endoscopic finding classification as the degree of progress, the processor outputs a discrimination result obtained by further subdividing the grade of the endoscopic finding classification.

3. The medical image processing apparatus according to claim 1,
wherein the second medical image is the medical image captured using the second illumination light with more blue or violet than the first illumination light.

4. The medical image processing apparatus according to claim 3, wherein the discrimination result of the lesion discriminated in the discrimination process is displayed on the monitor together with the superimposed information and the image.

5. The medical image processing apparatus according to claim 1,
wherein the one or more processors detect an inflammatory bowel disease or a cancer as the lesion.

6. The medical image processing apparatus according to claim 1,
wherein the one or more processors are configured to perform the discrimination process in a case where the type of the lesion in the detection process is a specific type.

7. The medical image processing apparatus according to claim 1,
wherein the one or more processors are configured to perform the discrimination process on the region where the lesion is detected in the detection process.

8. The medical image processing apparatus according to claim 1,
wherein the lesion includes at least one of inflammation related to an inflammatory disease, a polyp, redness, atrophy, diverticulum, or treatment scar.

9. An endoscope apparatus comprising:
a light source that emits a plurality of types of illumination light having different spectra; and
one or more processors configured to:
acquire a plurality of endoscopic images captured by alternately switching illumination light emitted from an endoscope to first illumination light and second illumination light having a spectrum different from the first illumination light;
perform a detection process of detecting a lesion by using a first endoscopic image captured using the first illumination light, among the endoscopic images;
perform a discrimination process of discriminating a type or a degree of progress of the lesion by using a second endoscopic image captured using the second illumination light, among the endoscopic images;
superimpose information indicating a position of the lesion detected in the detection process on an image captured using the first illumination light among the plurality of endoscopic images, and display the superimposed information and the image on a monitor; and
display a discrimination result of the lesion discriminated in the discrimination process on the monitor,
wherein the first endoscopic image is the medical image captured using white light,
wherein the second endoscopic image is the medical image captured using the second illumination light having a narrower wavelength band than the first illumination light.

10. A method of operating a medical image processing apparatus including one or more processors, the method comprising following steps, executed by the one or more processors, of:
acquiring a plurality of medical images captured by alternately switching illumination light emitted from an endoscope to first illumination light and second illumination light having a spectrum different from the first illumination light;
performing a detection process of detecting a lesion by using a first medical image captured using the first illumination light, among the medical images;
performing a discrimination process of discriminating a type or a degree of progress of the lesion by using a second medical image captured using the second illumination light, among the medical images;
superimposing information indicating a position of the lesion detected in the detection process on an image captured using the first illumination light among the plurality of medical images, and displaying the superimposed information and the image on a monitor; and
displaying a discrimination result of the lesion discriminated in the discrimination process on the monitor,
wherein the first medical image is the medical image captured using white light,
wherein the second medical image is the medical image captured using the second illumination light having a narrower wavelength band than the first illumination light.

11. The method of operating a medical image processing apparatus according to claim 10,
wherein the second medical image is the medical image captured using the second illumination light with more blue or violet than the first illumination light.

* * * * *